United States Patent [19]

Kastrubin et al.

[11] Patent Number: 4,724,841
[45] Date of Patent: Feb. 16, 1988

[54] APPARATUS FOR CENTRAL ELECTROANALGESIA

[75] Inventors: Eduard M. Kastrubin; Valentin M. Nozhnikov, both of Moscow; Sergei E. Aleshkov, Kaliningrad, all of U.S.S.R.

[73] Assignee: Moskovsky oblastnoy nauchnoissledovatelsky inst. akusherstva i ginekologii, Moskow, U.S.S.R.

[21] Appl. No.: 860,061

[22] Filed: May 6, 1986

[30] Foreign Application Priority Data

Jul. 18, 1983 [SU] U.S.S.R. ................................. 365001

[51] Int. Cl.$^4$ .............................................. A61N 1/36
[52] U.S. Cl. .................................. 128/420 R; 128/421; 128/791
[58] Field of Search .............. 128/1 C, 419 R, 420 R, 128/421, 422, 423 R, 791

[56] References Cited

U.S. PATENT DOCUMENTS

| | | | |
|---|---|---|---|
| 3,626,926 | 12/1971 | Kuzin et al. | 128/419 R |
| 3,958,577 | 5/1976 | Rudler | 128/420 X |
| 3,989,051 | 11/1976 | Nozhnikov et al. | 128/421 |
| 4,121,593 | 10/1978 | Kastrubin et al. | 128/421 |
| 4,140,133 | 2/1979 | Kastrubin et al. | 128/421 |
| 4,167,190 | 9/1979 | Sorenson et al. | 128/423 R |

Primary Examiner—William E. Kamm
Attorney, Agent, or Firm—Lilling & Greenspan

[57] ABSTRACT

An apparatus for central electroanalgesia comprises units for rhythmic action, which are connected in series with units for changing the shape of current pulses and preamplification units electrically coupled to a regulator of the amplitude of current pulses, a means for selecting a mode of action, a means for programmed limitation of the current average value, and a means for amplifying the output signal, which is connected, via a means for measuring the current average value, to electrodes secured on the patient's neck below the mastoid processes and on his forehead. The output signal amplifying means is connected to a compensation current limiting unit couple to a constant component compensating unit joined to a compensation current regulator.

1 Claim, 2 Drawing Figures

APPARATUS FOR CENTRAL ELECTROANALGESIA

FIELD OF THE INVENTION

This invention relates to medical equipment and, more particularly, to apparatuses for central electroanalgesia.

The invention can be used in anesthesiology for general electromedicamental anesthesia and in physiothrapy for electroacupuncture, transdermic electroneurostimulation, electrostimulation of organs and tissues.

PRIOR ACT

Known in the art is an apparatus for central electroanalgesia (cf., for example, App. No. 8,328,300 filed with the British Patent Office on Oct. 22, 1983), which comprises several series-connected units, namely a rhythmic action unit, a unit for independent and smooth adjustment of the pulse repetition frequency and duration of current pulses, a unit maintaining a constant period-to-duration ratio of pulses, a unit for adjusment of pulse duration, and a unit for changing the shape of current pulses, which is connected, via a mode switch, to a series-connected arrangement comprising a preamplification unit and an adder of the pulsed action and the additional constant component, which is connected to a unit for measuring the average current value, which is in turn connected to an anode and a cathode which are secured, respectively, on the patient's neck below the mastoid processes and on the patient's forehead, and also connected to a unit for measuring the amplitude of the current, whose output is connected to one of the inputs of the adder whose one output is connected to an input of a unit for programmed limitation of the current average value, one of the outputs thereof being connected to the preamplification unit, while the other output thereof is connected to an input of a unit for regulating the additional constant component, whose another input is connected to an output of a unit of the additional constant component of a power supply unit of all units enumerated above, and an output is connected to an adder, while the remaining input is connected to an individual switch connected to a regulator for preliminary setting of the additional constant component level and to a remote electroanalgesia unit which is coupled to individual switches connected, respectively, to regulators of the pulse recurrence rate and amplitude of current pulses, which are connected, respectively, to the rhythmic action unit and the preamplification unit, the rhythmic action unit being provided with an output to produce sawtooth voltage pulse trains, the apparatus also comprising a unit for preamplification of sawtooth voltage pulses, whose one input is connected to said output of the rhythmic action unit, while the other input thereof is connected to the power supply unit, a unit for varying the period-to-duration ratio of pulses and generating square pulses from sawtooth voltage pulses, which has its input connected to the output of the sawtooth voltage pulse preamplification unit, another input connected to the power supply unit, and its output connected, via a mode switch, to the current pulses preamplification unit, an individual switch connected, respectively, to an output of the remote electroanalgesia unit and to the remaining input of the unit for varying the period-to-duration ratio of pulses and generating square pulses from sawtooth voltage pulses, and a regulator of the period-to-duration ratio of pulses, which is connected to the switch connected to the unit for varying the period-to-duration ratio of pulses and generating square pulses from sawtooth voltage pulses.

The circuitry of this apparatus is deficient in that composite pulse trains cannot be used for anesthesiological purposes when a combination of amplitude and time characteristics of the output signal.

In consequence the clinical practice makes no use of the interference of pulse signals when two pulse oscillators are used in series or in parallel. This combined use can improve the effect of the apparatus action (cf., for example, U.S. Pat. Nos. 4,334,525 and 4,383,522 filed, respectively, on June 15, 1982 and May 17, 1983).

Combined pulse trains are known to have been used in anesthesiology in an apparatus for central electroanalgesia, which comprises two channels for pulsed action, comprising, respectively, several series-connected elements: rhythmic action units equipped with frequency regulators of current pulses, current pulse waveform control units equipped with regulators of the pulse period-to-duration ratio, and current pulse preamplification units, inputs of the current pulse preamplification units of each channel being electrically connected to a current pulse amplitude regulator, while the outputs thereof are electrically connected, one output directly and the other via a mode of action means electrically coupled to the remaining current pulse preamplification unit and to a means for programmed limitation of the average current value, to inputs of a means for outputs signal amplification, whose one output is connected to an input of the means for programmed limitation of the average current value, which has its outputs connected to some inputs of the current pulse preamplification units of each channel, while another output of the output signal amplification unit is connected to a means for measuring the average current value, which is connected to electrodes secured on the patient's neck below the mastoid processes and on the patient's forehead (cf., for example, application No. 2,154,449 filed with the British Patent Office, preexamination publication Sept. 11, 1985).

This apparatus can be useful in obtaining optimal results with minimal currents and voltages (prevention of convulsion activities). But the lengthy use of the direct current component in microsurgery produces an excessive polarization effect under the electrodes.

This means that the above described apparatus does produce the required effect of combined electro-anesthesia but fails to provide physical methods for elimination of excessive polarization effects which are due to the action of the direct pulsed current of the positive polarity and the varying direct current component (adjustment of the amplitude, frequency and duration of current pulses, increase of the additional direct current component).

In addition, this apparatus cannot be recommended for use for lengthy electrostimulation of biologically active points of organs and tissues in the course of transdermal electroneurostimulation.

There is known an apparatus, produced in France under the name of "Anestelec", which eliminates the above mentioned drawback using a maximum voltage of 300–400 mA. But the anesthetic properties of current have been seriously affected and additional administration of pharmacological anesthetics is required.

SUMMARY OF THE INVENTION

It is an object of this invention to eliminate the excessive polarization effects produced during electroanesthesia, provided the apparatus can be used for lengthy periods and a required level of pain relief is maintained.

The invention provides an apparatus for central electroanalgesia, which has two channels for pulsed action, comprising respectively several series-connected elements: rhythmic action units equipped with frequency regulators of current pulses, current pulse waveform control units equipped with regulators of the current pulse period-to-duration ratio, and current pulse preamplification units, inputs of the current pulse preamplification units of each channel being electrically connected to an amplitude regulator of current pulses, while the outputs thereof are electrically connected, one of said outputs directly and the other via a mode of action means which is electrically coupled with the remaining current pulse preamplification unit and to a means for programmed limitation of the average current value, to inputs of a means for amplifying the output signal, which has one of the outputs thereof connected to an input of the means for programmed limitation of the average current value, whose outputs are connected to one of the inputs of the current pulse preamplification units of each channel, while the other output of the output signal amplification means is connected to a means for measuring the average current value, which is connected to electrodes secured on the patient's neck below the mastoid processes and on the patient's forehead, which, according to the invention, is provided with a compensation current limiting unit whose input is connected to one of the outputs of the output signal amplification unit, a direct component compensating unit, which has its one input connected to an output of the compensation current limiting unit, while the output thereof is connected to one of the inputs of the output signal amplification means, and a compensation current regulator whose output is connected to another input of the compensation current limiting unit.

The apparatus for central electroanalgesia according to the invention permits elimination of the excessive polarization effects under the electrodes, which occur during lengthy operative interventions, when combined types of electroanesthesia are used.

BRIEF DESCRIPTION OF THE DRAWINGS

These and other objects of the invention will become apparent from the following description taken together with the accompanying drawings in which.

DETAILED DESCRIPTION OF THE INVENTION

Figure 1:
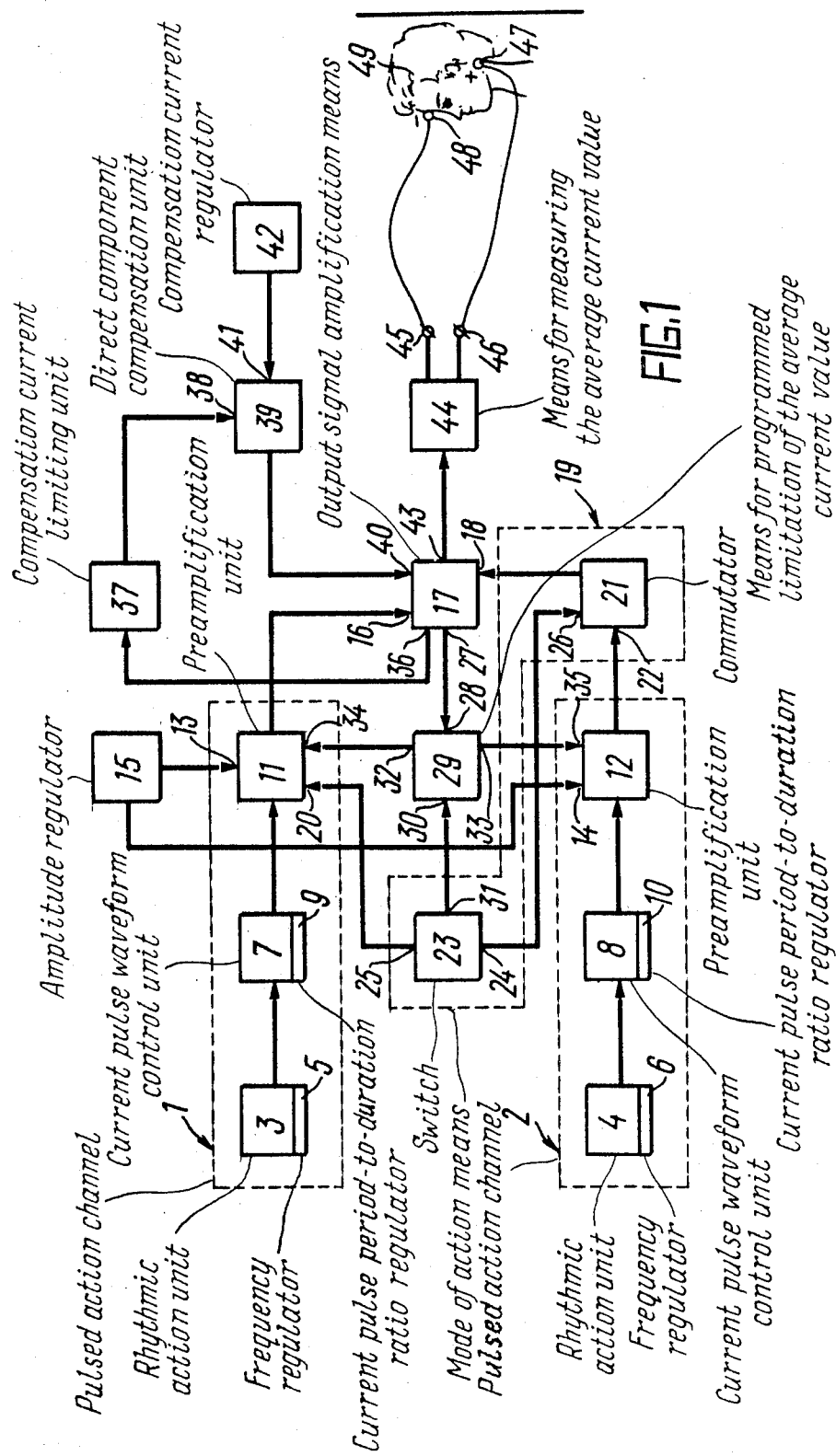
FIG. 1 shows a block diagram of an apparatus for central electroanalgesia, according to the invention.

An apparatus for central electroanalgesia, according to the invention, comprises two channels 1 (FIG. 1) and 2 for pulsed action. Channels 1 and 2 comprise, respectively, rhythmic action units 3 and 4 equipped with frequency regulators 5 and 6 of current pulses, current pulse waveform control unit 7 and 8 equipped with regulators 9 and 10 of the current pulse period-to-duration ratio, and unit 11 and 12 for preamplification of current pulses. All these units are connected in series.

Inputs 13 and 14 of the units 11 and 12 are connected to outputs of an amplitude regulator 15 of current pulses. An output of the unit 11 is connected to an input 16 of an output signal amplification means 17. An output of the unit 12 is electrically connected to an input 18 of the output signal amplification means 17 via a mode of action means 19 which is electrically coupled with an input 20 of the preamplification unit 11.

The mode of action means 19 comprises a function commutator 21 whose input 22 is connected to an output of the preamplification unit 12, while the output thereof is connected to the input 18 of the output signal amplification means 17, and a function switch 23 whose outputs 24 and 25 are connected, respectively, to an input 26 of the commutator 21 and to the input 20 of the unit 11.

An output 27 of the output signal amplification means 17 is connected to an input 28 of a means 29 for programmed limitation of the average current value, another input 30 thereof being connected to an output 31 of the switch 23, while outputs 32 and 33, respectively, are connected to inputs 34 and 35 of the units 11 and 12.

An output 36 of the output signal amplification means 17 is connected to an input of a compensation current limiting unit 37 whose output in turn is connected to an input 38 of a direct component compensating unit 39 whose output is connected to an input 40 of the amplification means 17. An input 41 of the unit 39 is connected to an output of a compensation current regulator 42.

An output 43 of the amplification means 17 is connected to a means 44 for measuring the average current value, which is connected, via terminals 45 and 46, to a pair of electrodes 47 and 48, which are a split anode and a split cathode. The electrodes 47 and 48 are secured, respectively, on the patient's neck under the mastoid processes and on the patient's forehead. The electrodes 47 and 48 are made in a conventional way known to all persons skilled in the art.

The circuit of the apparatus according to the invention is made as follows.

The rhythmic action unit 3 is a self-sustained sawtooth voltage oscillator built around a unijunction transistor 50, resistors 51 and 52, and a capacitor 53. The frequency regulator 5 is an adjustable resistor 54. The current pulse period-to-duration ratio regulator 9 is an adjustable resistor 55. The current pulse waveform control unit 7 is a comparison circuit with an adjustable threshold based on an operational amplifier 56 and resistors 57 and 58. The amplitude regulator 15 is a double level regulator based on adjustable resistors 59 and 60. The preamplification unit 11 is an integrated transistor array 61 and resistors 62, 63 and 64.

The amplification means 17 uses integrated transistor arrays 65 and 66, and resistors 67, 68, 69 and 70. The means 44 is a meter 77 for measuring the average current value. The means 29 for programmed limitation of the average current value is built around integrated transistor arrays 72 and 73, resistors 74, 75 and 76, and a capacitor 77.

The switch 23 is a double-throw switch 78 combined in fours. The unit 12 uses an integrated transistor array 79, and resistors 80 and 81. The commutator 21 is a differential amplifier built around an integrated transistor array 82 and resistors 83 and 84.

The current pulse waveform control unit 8 is a comparison circuit having an adjustable threshold and built around an operational amplifier 85 and resistors 86 and 87. The regulator 10 of the current pulse period-toduration ratio is an adjustable resistor 88. The frequency regulator 6 is an adjustable resistor 89. The rhythmic action unit 4 is a self-sustained sawtooth voltage oscillator built around a unijunction transistor 90, resistors 91 and 92 and also a capacitor 93.

The compensation current regulator 42 is built around a resistor 94 and an adjustable resistor 95. The direct component compensating unit 39 uses integrated transistor circuits 96 and 97, and resistors 98 and 99. The compensating current limiting unit 37 is built around an integrated transistor circuit 100, resistors 101 and 102, and a capacitor 103.

Units and means of the apparatus are supplied with power through lines 104, 105, 106 and 107.

Figure 2:
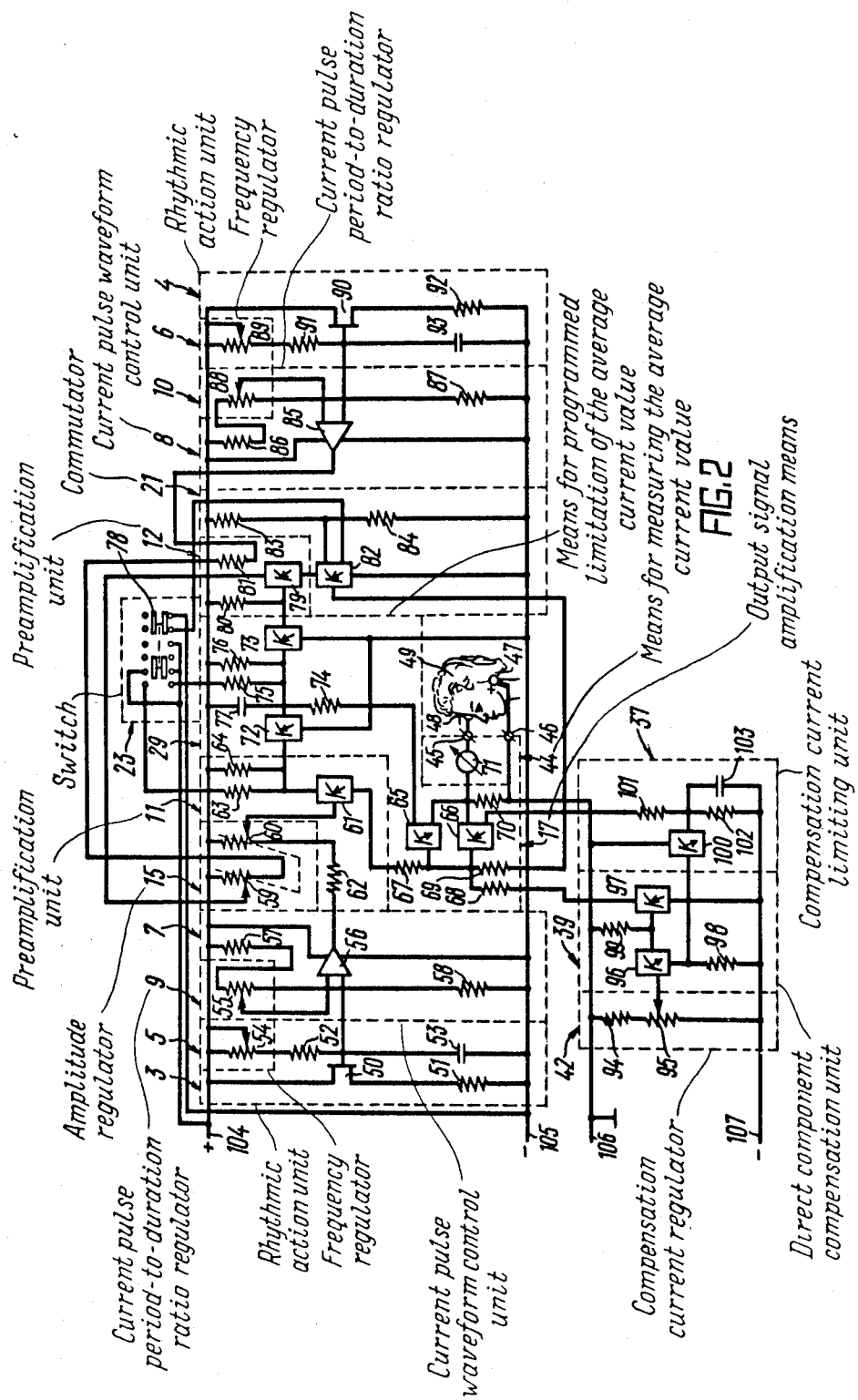
FIG. 2 shows a schematic circuit diagram of the apparatus of FIG. 1.

Electrical connections between the elements enumerated in the description of FIG. 2 are as follows.

The adjustable transistor 54 is connected to the resistor 52 of the unit 3. The adjustable resistor 55 is connected to the resistors 57 and 58, and to the input of the operational amplifier 56 of the unit 7.

The adjustable resistor 59 is connected to the integrated transistor circuit 79 and to the resistor 81 of the unit 12. The adjustable resistor 60 is connected to the resistor 62 and to the integrated transistor circuit array 61 of the unit 11.

The resistor 62 is connected to the operational amplifier 56 of the unit 7.

The integrated array 65 is connected to the resistor 74 of the means 29. The integrated transistor array 66 is connected to the resistor 101 of the unit 37. In addition, the integrated arrays 65 and 66 are connected to the average current value meter 71, the resistor 67 of the means 17 being coupled with the integrated transistor array 61 of the unit 11. The resistor 68 is connected to the integrated transistor array 97 of the unit 39, while the resistor 69 is connected to the integrated transistor array 82.

The integrated array 72 is connected to the integrated array 61 and resistors 63 and 64 of the unit 11 to form a differential amplifier. The integrated array 73 is connected to the integrated array 79 and to the resistor 80 of the unit 12 and also forms a differential amplifier.

The resistor 75 is connected to the double-throw switch 78.

The resistor 81 is connected to the output of the operational amplifier 85 of the unit 8, while the integrated array 79 is connected to the integrated array 82.

The integrated array 82 is connected to a double-throw switch 78. The operational amplifier 85 is connected to the adjustable resistor 88 and to the base of the unijunction transistor 90 of the unit 4, at the point where said base is connected to the resistor 91 and the capacitor 93. The resistors 86 and 87 of the unit 8 are connected to the adjustable resistor 88. The adjustable resistor 89 is coupled with the resistor 91 of the unit 4.

The adjustable resistor 95 is connected to the integrated transistor array 96 of the unit 39. The integrated transistor array 96 is connected to the integrated array 100 of the unit 37 to form a differential amplifier. The integrated transistor array 100 is connected to the resistors 101 and 102 and the capacitor 103.

The apparatus for central electroanalgesia according to the invention operates as follows.

For general electromedicamental anesthesia, a mask of rubber bands is put on the head of the patient 49 (FIG. 1) to secured two pairs of electrodes 47 and 48. The first pair is fitted on the patient's forehead (split cathode), while the second pair is fit on the patient's neck under the mastoid processes (split anode).

Anesthesia during surgical operations is conducted after standard premedication, intubation, introduction of relaxants, artificial pulmonary ventilation by a gas mixture composed of nitrous oxide and oxygen taken in a ratio of 2 to 1 or 1 to 1.

The main component of the general anesthesia is pulsed current which is produced in the unit 3. The regulator 5 is used to set the required frequency of pulses. After that, the regulator 9 of the unit 7 is used to set the specific period-to-duration ratio of the current pulses, which determines the depth of action. The regulator 15 is used to make a preliminary setting of the amplitude of current pulses in the unit 11.

The signal thus produced is amplified in the means 17 and supplied, via the average current measuring means 44, to the electrodes 48 and 47.

If inadequacy of anesthesia is manifested by such clinical signs as tachycardia and hypertension, the level of general anesthesia can be made deeper without resorting to additional introduction of anesthetics. The apparatus can be used to obtain this effect by employing combined pulse trains. To this end, the pulsed action channel 2 is connected to the means 17 with the aid of the switch 23 and commutator 21. The pulse repetition frequency in the channel 2 is stepped up by the unit 4 and the regulator 6. The regulator 10 is used to obtain a specific period-to-duration ration of current pulses in the unit 8, while the regulator 15 is used to provide preamplification of the amplitude of the current pulse sequence in the unit 12. This current pulsesequence is supplied, via the commutator 21, to the input 18 of the output signal amplification means 17 where a combined pulse train is produced as a result.

In physiotherapy electrostimulation of organs and tissues is known to be conducted by signals devoid of the direct current component. This apparatus also provides for a mode of operation without the direct current component in order to make its field of application broader. But in contrast to the prior art apparatuses, this apparatus is capable, in addition to the elimination of the direct current component, to provide adjustment of the pulse amplitude and, also, of the recurrence rate and the period-to-duration ratio. It becomes possible to perform physiotheraputic procedures adapted to individual peculiarities of an organism.

For this purpose, the apparatus comprises a direct current component compensating unit 39 and a compensation current regulator 42. To achieve a specific mode of action, the direct current component is measured by the means 44 and compensated to a required degree. The patient is protected by an automatic system for controlling the level of the average current by the means 29 and the unit 37.

When the direct component is to be used, the regulator 42 is smoothly brought back to the initial position.

The apparatus according to the invention is, consequently, a universal device which combines anesthetic action (central electroanalgesia, general electromedicamental anesthesia), treatment (central electrotherapy), and therapeutic electrostimulation of organs and tissues (electroacupuncture, transdermal electroneurostimulation).

Specific narrow terminology is used in the description of the preferred embodiment of the invention for clarity's sake. However, the invention is in no way limited to the terminology thus adopted and it should be remembered that each such term is used to denote all equivalent elements functioning in an analogous way and employed for similar purposes.

While the invention has been described herein in terms of the preferred embodiments, it is understood that numerous variations may be made without deviating from the idea and scope of the invention, which is apparent to those skilled in the art.

These changes and variants may be made without exceeding the spirit and scope of the invention and appended claim given below.

What is claimed is:

1. An apparatus for central electroanalgesia, comprising:

a first pulsed action channel comprising;

a first rhythmic action unit having an individual regulator of current pulse frequency and an output, a first current pulse waveform control unit having an individual regulator of the current pulse period-to-duration ratio, an input connected to said output of said first rhythmic action unit, and an output, a first current pulse preamplification unit having a first input connected to said output of the first current pulse waveform control unit, a second input, a third input, a fourth input, and an output;

a second pulsed action channel comprising;

a second rhythmic action unit having an individual regulator of the current pulse frequency, and an output, a second current pulse waveform control unit having an individual regulator of the current pulse period-to-duration ratio, an input connected to said output of the second rhythmic action unit, and an output;

a second current pulse preamplification unit having a first input connected to said output of the second current pulse waveform control unit, a second input, a third input, and an output;

a current pulse amplitude regulator having a first output connected to the second input of the first current pulse preamplification unit, and a second output connected to the second input of the second current pulse preamplification unit;

a mode of action means having a first input connected to said output of the second current pulse preamplification unit, a first output connected to the fourth input of the first current pulse preamplification unit, a second output, and a third output;

a means for programmed limitation of the average current value, which has a first input connected to the second output of said mode of action means, a second input, a first output connected to the fourth input of the first current pulse preamplification unit, and a second output connected to the third input of the second current pulse preamplification unit;

an output signal amplification means having a first input connected to said output of the first current pulse preamplification unit, a second input, a third input connected to the third output of said mode of action means, a first output connected to the second input of said means for programmed limitation of the average current value, a second output, and a third output;

a compensation current limiting unit having an input connected to the second output of said output signal amplifying means, and an output;

a direct component compensating unit having a first input connected to said output of said compensation current limiting unit, a second input, and an output connected to the second input of said output signal amplifying means;

a compensation current regulator having an output connected to the second input of said direct component compensating unit;

a means for measuring the average current value, which has an input connected to the third output of said output signal amplifying means, and an outputs; and electrodes connected to said outputs of said means for measuring the average current value and secured on the patient's neck under the mastoid processes and on the patient's forehead.

* * * * *